United States Patent [19]

Gupta

[11] Patent Number: 5,563,061
[45] Date of Patent: Oct. 8, 1996

[54] METHOD FOR REPRODUCING CONIFERS BY SOMATIC EMBRYOGENESIS USING A MALTOSE ENRICHED MAINTENANCE MEDIUM

[75] Inventor: Pramod K. Gupta, Federal Way, Wash.

[73] Assignee: Weyerhaeuser Company, Federal Way, Wash.

[21] Appl. No.: 451,945

[22] Filed: May 26, 1995

Related U.S. Application Data

[63] Continuation-in-part of Ser. No. 203,090, Feb. 28, 1994, abandoned, which is a continuation-in-part of Ser. No. 156,482, Nov. 23, 1993, abandoned, which is a continuation-in-part of Ser. No. 814,976, Dec. 23, 1991, Pat. No. 5,294,549, which is a continuation-in-part of Ser. No. 705,681, May 24, 1991, Pat. No. 5,236,841, which is a continuation-in-part of Ser. No. 499,151, Mar. 26, 1990, Pat. No. 5,036,007, which is a continuation-in-part of Ser. No. 321,035, Mar. 9, 1989, Pat. No. 4,957,866, and a continuation-in-part of Ser. No. 426,331, Oct. 23, 1989, Pat. No. 5,034,326.

[51] Int. Cl.$^6$ .............................. A01H 4/00; A01H 7/00; C12N 5/04

[52] U.S. Cl. .................. 435/240.45; 435/240.4; 435/240.48; 435/240.49; 435/240.54; 800/200; 800/DIG. 49; 800/DIG. 50; 800/DIG. 51; 47/58

[58] Field of Search .................. 800/200; 435/240.4, 435/240.45, 240.49, 240.50, 172.1

[56] References Cited

U.S. PATENT DOCUMENTS

| | | | |
|---|---|---|---|
| 4,801,545 | 1/1989 | Stuart et al. | 435/240.45 |
| 5,036,007 | 7/1991 | Gupta et al. | 435/240.45 |
| 5,187,092 | 2/1993 | Uddin | 435/240.45 |
| 5,236,841 | 8/1993 | Gupta et al. | 435/240.45 |
| 5,413,930 | 5/1995 | Becwar et al. | 435/240.49 |

OTHER PUBLICATIONS

Nagmani, R. and R. J. Dinus. Paper at 21st Southern Tree Improvement Conference, Knoxville, TN, Jun. 17–20, 1991.
Schuller, Astrid and Gerhard Reuther. *Plant Cell Reports* 132: 199–202 (1993).
Strickland, Steven G., James W. Nichol, Carol M. McCall, and David A. Stuart. *Plant Science* 48: 113–121 (1987).
Tremblay, Laurence and Francine M. Tremblay. *Plant Cell, Tissue and Organ Culture* 27: 95–103 (1991).

*Primary Examiner*—Gary Benzion

[57] ABSTRACT

The invention is a method for reproducing coniferous trees by somatic embryogenesis using plant tissue culture techniques in a multistage culturing process. A suitable explant, typically the fertilized embryo excised from an immature seed, is first cultured on a medium that induces multiple early stage proembryos. These are multiplied in a second culture having reduced growth hormones. Maltose is supplied as the carbon and energy source in the second culture. Alternatively, a sucrose-containing maintenance and multiplication medium may be used followed by at least two subcultures on a maltose based maintenance medium. The early stage embryos grow in size and vigor to advanced early stage embryos. The embryos are then transferred to a cotyledonary embryo development culture. After several weeks somatic embryos having the appearance of zygotic embryos will have formed. These may be germinated before or after storage and transplanted to soil for further growth. Maltose used in the maintenance and multiplication culture results in larger and more robust advanced early stage embryos which, in turn, produce cotyledonary embryos very similar in morphology to natural zygotic embryos. The use of maltose at earlier stages of embryo development is more important than its use for embryo maturation.

24 Claims, 4 Drawing Sheets

METHOD FOR REPRODUCING CONIFERS BY SOMATIC EMBRYOGENESIS USING A MALTOSE ENRICHED MAINTENANCE MEDIUM

This invention is a continuation-in-part of earlier application Ser. No. 203,090, filed Feb. 28, 1994, now abandoned, which was a continuation-in-part of Ser. No. 156,482, filed Nov. 23, 1993 and now abandoned, which was a continuation-in-part of Ser. No. 814,976, filed Dec. 23, 1991 and now U.S. Pat. No. 5,294,549, which was a continuation-in-part of application Ser. No. 705,681, filed May 24, 1991 and now U.S. Pat. No. 5,236,841. That was a continuation-in-part of application Ser. No. 499,151, filed Mar. 26, 1990, now U.S. Pat. No. 5,036,007. This was in turn a continuation-in-part of application Ser. No. 321,035, filed Mar. 9, 1989, now U.S. Pat. No. 4,957,866 and Ser. No. 426,331, filed Oct. 23, 1989, now U.S. Pat. No. 5,034,326.

BACKGROUND OF THE INVENTION

The present invention is a method for reproducing coniferous plants by somatic embryogenesis using the techniques of plant tissue culture. More specifically, it relates to the use of a selected sugar as energy source in the culture media used during specific stages of somatic embryo development. The invention is especially suited for producing large numbers of clones of superior selections useful for reforestation.

Loblolly pine (*Pinus taeda* L.), its closely related southern pines, and Douglas-fir (*Pseudotsuga menziesii* (Mirb.) Franco) are probably the most important commercial species of temperate North American timber trees. Similarly, Norway spruce (*Picea abies* (L.) Karst.) is probably the most important European softwood species. Since the early 1940s, when serious private reforestation efforts began, literally billions of one and two year old nursery-grown trees have been planted on cut-over or burned forest lands. For many years these seedling trees were grown using naturally produced seed from cones collected as a part time effort of individuals seeking to supplement their incomes. As early as 1957 forest geneticists began to plant seed orchards using either seed or grafted scions obtained from superior trees discovered in the forests. These trees were selected for such heritable characteristics as rapid growth, straightness of bole, wood density, etc. Now in both the southern pine and Douglas-fir regions the bulk of the seed is produced from selected trees grown in seed orchards, some of them now second and third generation orchards.

Despite the fact that the orchards were stocked with superior trees, pollination often cannot be carefully controlled and frequently the seed trees are fertilized by wild pollen of unknown characteristics. For this reason, the characteristics of the progeny produced by sexual reproduction have not been as predictable as hoped and genetic gain could not be attained as rapidly as desired.

Beginning about 1960, techniques were developed for reproducing some species of plants by tissue culture. These were predominately angiosperms and usually ornamental house plants. The method employed use of a suitable explant or donor tissue from a desirable plant. This was placed on a series of culture media in which nutrients and growth hormones were carefully controlled from step to step. The usual progression was growth from the explant to a callus. The callus was placed on a budding medium where adventitious buds formed. These, in turn, were separated, elongated, and rooted to ultimately form plantlets. A plantlet has the nature of a seedling but is genetically identical to the explant donor plant.

Gymnosperms in general, and most forest tree species in particular, proved to be much more difficult to reproduce by tissue culture. It was not until about 1975 that Douglas-fir was successfully reproduced by organogenesis. Loblolly pine was successfully reproduced about two years later.

A brief review of some of the most important work relating to the present invention will follow. This is intended to be representative only and is not fully inclusive of all the work in the field. Literature citations in the text are given in abbreviated form. Reference should be made to the bibliography at the end of the specification for full citations of the literature noted herein.

Culture by organogenesis is tedious and expensive due to the large amount of delicate manual handling necessary. It was soon recognized that embryogenesis was potentially a much more desirable method from the standpoints of quantity of plantlets produced, cost, potential genetic gain, and much lower probability of mutations. Work on embryogenesis of forest species began in the late 1970s. U.S. Pat. No. 4,217,730 to El-Nil describes one early attempt at somatic embryogenesis of Douglas-fir. This approach was later set aside because advanced stage embryos and plantlets could not be readily obtained. However, other workers entered the field in increasing numbers and progress has been rapid even if it has not until the present time reached the commercial stage.

Earlier U.S. Pat. Nos. 4,957,866, 5,034,326, 5,036,007, and 5,236,841, herein incorporated by reference, describe improved methods of conifer embryogenesis. These also include extensive reviews of the most closely related literature. In the methods described in all of these patents, advanced early stage embryos (or "late stage proembryos"), defined as totipotent embryonic structures estimated to have least about 100 mostly undifferentiated cells, are transferred to and further cultured in a cotyledonary embryo development medium containing abscisic acid (ABA) as an essential growth hormone. It appears to be highly desirable during this stage to gradually reduce the level of exogenous ABA so that little or none is ultimately present. Other growth hormones; e.g., gibberellins, may also be used at this time. The ultimate product of this culturing step is somatic embryos resembling natural zygotic embryos in morphology.

It is well accepted that plant tissue culture is a highly unpredictable science. Sondahl et at., in published European Patent Application 293,598, speak directly to this point.

"Since each plant species appears to possess a unique optimal set of media requirements, the successful preparation and regeneration of a new species cannot be necessarily inferred from the successful regimens applied to unrelated plant species."

This statement can be carried even farther. Rangaswamy (1986) notes that the potential for embryogenesis is even genotype specific within any given species.

Compositions of the media used to initiate embryogenesis and induce embryo maturation are critical to success, regardless of the species being propagated. In particular, the type and level of the nitrogen source in the media and the presence or absence, composition, level, and timing of availability of growth hormones have been the key to success. It is also these very factors, particularly the hormones, that have proved to be so unpredictable. As one example, Ammirato (1977), conducted a study examining the effects of zeatin (a cytokinin), ABA, and gibberellic acid ($GA_3$) on the yield and morphology of caraway (*Carum*

*carvi*) somatic embryos. These hormones were present singly and in all possible combinations in the media used for the later stages of embryo development. He concluded that a change in level or presence/absence of any one of the hormones caused a ripple effect felt throughout the system due to unpredictable interactions between the various hormones. Lakshmi Sita (1985) summarizes her earlier work and that of others in promoting embryogenesis of sandalwood (Santalum sp.). Gibberellic Acid was found to be useful in inducing embryogenesis using shoot explants in either solid or liquid suspension cultures. Despite her success, which included successful production of converted plants, she again points to the lack of predictability of embryogenesis.

"Despite progress, our knowledge of embryogenesis is still fragmentary. At present we cannot yet define the conditions necessary for embryogenesis . . . "

The same problem is again discussed by Evans (1984) who notes that growth hormones which affect the same process can either act independently or may interact in some fashion.

In general, as far as coniferous species are concerned, it appears that at least one exogenous auxin and usually a cytokinin are necessary hormones in a medium for the initiation of embryogenesis. While much work has been done studying the effect of the stimulatory growth hormones, and the effect of the nitrogen source in the media, little consideration has been given to the carbohydrate used as the carbon and energy source for the growing embryos. It has been known that various sugars were metabolized by developing embryos; e.g., U.S. Pat. No. 5,036,007 suggests that sucrose, glucose, fructose, maltose or galactose are metabolizable and suitable for osmotic potential control in cotyledonary embryo development media. These were used alone or in combination with poorly metabolized materials such as polyalkylene glycols. However, it has been generally assumed by most workers that sucrose or glucose were optimal.

Stuart et al., in U.S. Pat. No. 4,801,545, note that "maltose has been used in several studies of plant growth and differentiation without success" and cite several references to this effect. However, they found that about 90 mM of maltose in combination with at least one amino acid chosen from the group of proline, alanine, or glutamine increased the number of embryos produced in alfalfa cultures. In a closely related article, Strickland et al. (1987) noted that maltose, maltotriose, and soluble starch all acted to improve embryo morphology and conversion in alfalfa cultures. The presence of ammonium ion ($NH_4^+$) was said to be essential with maltose in order to see the improvement.

Uddin, in U.S. Pat. No. 5,187,092, describes somatic embryogenesis of loblolly pine using glucose or maltose in combination with abscisic acid in the mature embryo development medium. The data available in the Uddin patent are very limited. However, it appears that a two stage treatment in which the ABA level is increased and the auxin indolebutryic acid is added to the second stage is necessary if the claimed improvements are to be achieved. The high level of ABA and the stepwise increase are at odds with others in the field who have found that ABA is needed at relatively low levels which should preferably be decreased during the development period; e.g. as taught in U.S. Pat. Nos. 5,034,326 and 5,236,841.

Nagmani and Dinus ((1991) use a procedure similar to that of Uddin by employing maltose in the cotyledonary embryo development stage but with Douglas-fir rather than loblolly pine.

More recently, Beewar et at., in U.S. Pat. No. 5,413,930, teach the use of maltose in cotyledonary embryo development medium for Pinus species.

Tremblay and Tremblay (1991) explored various carbohydrate sources in the cotyledonary development (or maturation) medium for black spruce (*Picea mariana*) and red spruce (*Picea rubens*) embryos taken from a maintenance culture. Maltose was found to be about equivalent to glucose or sucrose for red spruce and much inferior to glucose or sucrose in promoting mature embryo development in black spruce. These investigators concluded that "different spruce species have varying carbohydrate requirements for the development of somatic embryos".

Schuller and Reuther (1993) looked at a similar selection of carbohydrate energy sources for developing embryos of European silver fir (*Abies alba*), although they substituted soluble starch for maltose. Soluble starch and lactose were found to be most effective at the later stages of cotyledonary embryo development.

Techniques to promote embryogenesis of numerous conifer genera are now well established. Research emphasis is now shifting to development of ways to scale up laboratory knowledge and techniques so that the process may become field operational on large scale. Yet many problems of a relatively fundamental nature still remain to be solved. One of these is improving somatic embryo quality and vigor. This is necessary so that germination to hardy plantlets and ultimate conversion to growing trees can be achieved at much higher percentages than has heretofore been possible. As workers gain more experience in conifer embryogenesis it has become evident that well formed advanced early stage embryos entering the development stage are a critical necessity for production of vigorous and well developed cotyledonary embryos. Reference might be made to U.S. Pat. No. 4,957,866 in this regard. The present invention is directed to this end.

SUMMARY OF THE INVENTION

The present invention is directed to the use of a particular sugar as the carbon and energy source in the media used at the different stages of conifer embryogenesis. It is especially directed to the use of the sugar maltose in the maintenance media used following embryo initiation by somatic embryogenesis. The replacement of the sucrose or glucose normally used at this stage of culture by maltose results in larger and more robust advanced early stage embryos of generally improved morphology. Maltose is also advantageously used in place of sucrose in the medium when a singulation step is found useful between the early stage embryo development and cotyledonary embryo development stages. This step is preferably used with Douglas-fir where the early stage embryos tend to form in dumps, some of which may persist throughout the rest of the culturing procedure.

The present method is especially suitable for reproducing woody gymnosperms of the order Coniferales. It is particularly well suited for generating large clones of superior forest trees for reforestation, including species within the families Pinaceae, Cupressaceae, and Taxodiaceae. Most or all species within the genera Abies, Pinus, Picea, Tsuga, Pseudotsuga, Thuja, Juniperis, Larix, Taxus and Sequoia are believed to be amenable to multiplication by the present method.

The method is particularly advantageous in that it ultimately enables more robust somatic embryos to be produced. These have a high degree of similarity to the natural zygotic embryos produced within the seed. This results in higher numbers of embryos that can be successfully converted into plants growing in soil. Costs per plant can be significantly reduced over prior known tissue culture methods. In addition, use of the method generates early stage embryos that can be retained for extended periods of time in cryogenic storage. Alternatively, cotyledonary embryos are produced that can be held in cold storage for prolonged periods without the need to transfer them from the development medium.

A number of terms are known to have differing meanings when used in the literature. The following definitions are believed to be the ones most generally used in the field of botany and are consistent with the usage of the terms in the present specification.

"Auxins" are plant growth hormones that promote cell division and growth.

"Cytokinins" are plant growth hormones that affect the organization of dividing cells.

"Callus" is generally considered to be a growth of unorganized and either unconnected or loosely connected plant cells generally produced from culturing an explant.

"Embryogenic callus" is a translucent white mucilaginous mass that contains early stage embryos attached to suspensors. This is also referred to as an "embryonal-suspensor mass" or "ESM" by some investigators.

An "early stage embryo", also sometimes referred to as a proembryo before elongation of suspensor, is a small mass of cells with dense cytoplasm and large nuclei that have the potential of forming a plant. The early stage embryo is normally found as a head having a relatively small number of undifferentiated dense cells with large nuclei associated at the end of one or more long thin-walled suspensor cells.

An "advanced early stage embryo" is larger than an early stage embryo and has a smooth embryonal head associated with multiple suspensor cells. The advanced early stage embryo is much more robust than an early stage embryo. Advanced early stage embryos generally show no or only the initial stages of internal cell differentiation when sectioned.

A "cotyledonary embryo", sometimes simply referred to as an "embryo", has a well defined elongated bipolar structure with latent meristematic centers having clearly visible cotyledonary primordia surrounding and usually obscuring an apical dome at one end and a latent radicle at the opposite end. The cotyledonary structure frequently appears as a small "crown" at one end of the embryo. A cotyledonary somatic embryo is analogous to a zygotic embryo.

A "mature embryo" is a cotyledonary embryo with adequate storage material (proteins, lipids, and carbohydrates) so as to be tolerant to desiccation.

An "explant" is a piece of tissue taken from a donor plant for culturing.

A "meristem" or "meristematic center" is a group of tissue forming cells capable of further development into plant organs; e.g., shoots and roots.

An "osmoticant" or "osmoticum" is a chemical material used for controlling the osmotic potential of a solution. In the present context the solution would be a culture medium.

A "plantlet" is a plant asexually reproduced by tissue culture.

A "converted embryo" is an embryo that has germinated and been established as a plant growing in soil.

"Somatic embryogenesis" is the process using tissue culture techniques for generating multiple embryos from an explant. The embryos generated from a given tissue source are believed to be genetically identical.

The present method as a whole comprises a multistage culturing process. A suitable explant is first placed on an induction or initiation culture medium. This will usually contain relatively high quantities of growth hormones including at least one auxin and frequently one or more cytokinins. However, with some species growth hormones at this initial stage may not always be necessary or desirable for induction of early stage embryos. A number of sources of explants have in the past proved to be satisfactory for culturing. These include, but are not limited to, tissue from cotyledons, hypocotyls, epicotyls, buds, meristematic centers for buds or roots, and seed embryos. Zygotic embryos removed from seeds are presently preferred. These may or may not include the surrounding gametophyte. In particular, for species which before have proved to be very difficult or impossible to propagate by somatic embryogenesis, the embryos from immature seeds may be preferred.

The first stage induction or initiation medium will normally be one of those well known from past work which contain a balanced concentration of inorganic salts and organic nutrient materials, with plant growth hormones included as noted above. Auxins are normally present in concentrations which may initially be as high as about 600 $\mu$M/L, more typically not exceeding about 500 $\mu$M/L. Cytokinins, if present, may initially be as high as 500 $\mu$M/L. The plant growth hormones may include at least one auxin and one cytokinin in a combined initial concentration not exceeding about 1100 $\mu$M/L, more typically not exceeding about 900 $\mu$M/L. The particular auxins and cytokinins used and their exact concentrations, or whether they are used at all, will depend somewhat on the species being cultured and even on the particular genotype within that species. This is something that cannot be easily predicted but can be readily determined experimentally. These very high levels of growth hormones assume the presence in the medium of an adsorbent material, such as activated charcoal. Where charcoal is not present the levels of growth hormones would normally be much lower; e.g., a full order of magnitude, than those just noted.

Culturing during the induction or initiation stage may be carried out in the dark, under very low light conditions, or in full light until an embryogenic mass forms. Lighting conditions will depend in large part on the composition of the particular medium selected. In general, initiation in full dark is preferred. This embryogenic mass has been described by various other names by researchers who have reported it in the past; e.g., embryogenic callus (Hakman and yon Arnold 1985) or embryonal-suspensor mass (Durzan and Gupta 1987). It has the appearance of a whitish, translucent, mucilaginous mass containing very small early stage embryos which are readily apparent by low power light microscopy (FIG. 1). In the case of Douglas-fir the presence of activated charcoal or a similar adsorbent in the initiation medium appears to be quite advantageous. It should be noted here that Douglas-fir does not experience polyembryony in the same manner as do most other coniferous species. The reasons for this are not well understood but one hypothesis suggests that Douglas-fir seeds contain a high endogenous level of abscisic acid which suppresses polyembryony. Activated charcoal in the initiation medium may remove this endogenous ABA, as well as other undesirable metabolic byproducts, to allow polyembryony to occur in vitro. Because the charcoal will also gradually remove growth hormones over time the initial concentrations of these materials are necessarily higher than might otherwise be the case.

The preferred induction medium for Douglas-fir will preferably contain an auxin or auxins in amounts of about 400–600 μM/L and a cytokinin or cytokinins in the amount of about 240–500 μM/L in combination with 0.05–1.0% activated charcoal.

Early stage embryos from the first culture are normally transferred to a maintenance and multiplication medium of higher osmotic potential than the induction medium. This multiplication medium will typically have the concentration of plant hormones significantly reduced below that of the induction medium. By "significantly reduced" is meant lowered by a factor which may typically be one whole order of magnitude. In the case of Douglas-fir it may be two full orders of magnitude below that initially present in a charcoal containing induction medium. No hormone adsorbent is usually necessary or desirable at this time. Especially for species such as loblolly pine (*Pinus taeda*) and Douglas-fir (*Pseudotsuga menziesii*) the osmotic potential of the maintenance medium should be significantly increased over that of the induction medium.

It is desirable that the early stage embryos formed in the initiation medium should be further enlarged in the maintenance and multiplication medium. To help achieve this the osmotic potential will most usually exceed about 160 mM/kg and will more typically be above about 180–200 mM/kg. The optimum osmoticant levels at each stage will usually differ for each species and often for individual genotypes within a species. For loblolly pine the osmotic level should typically be of the magnitude of at least 180 mM/kg and preferably about 200 mM/kg or even higher. However, lower levels of about 170 mM/kg minimum will suffice for most genotypes of Douglas-fir. One advantage of this osmotic "pulse" is that it contributes to embryo quality and size with the development of advanced early stage embryos (FIG. 2). Some species such as Norway spruce, which are relatively easy to reproduce, may not require this raised osmotic level, or it may only be necessary for some genotypes. In these cases advanced early stage embryo development may usually be achieved without a change in medium composition other than reduced hormone concentrations. Usually weekly subcultures are made when the embryos are on maintenance medium.

In virtually all work reported to date sucrose has been employed as the carbon or energy source in the maintenance medium. Surprisingly, it has now been discovered that maltose is much to be preferred to sucrose. Advanced early stage embryos produced using maltose in the maintenance medium have significantly larger embryonal heads than those produced using sucrose. These are both longer and of greater diameter. The associated suspensor cells are also elongated more. This results in stronger embryos that, in turn, produce more robust cotyledonary somatic embryos having close similarity to zygotic embryos.

Incubation at this stage is usually carried out in the dark or in greatly reduced light until robust advanced early stage embryos have formed. Subcultures are usually carried out on a weekly basis at this stage. The embryos may then be transferred to a cotyledonary embryo development medium which usually lacks auxins and cytokinins entirely.

Many investigators refer to cotyledonary embryo development from early stage embryos simply as a "maturation" or "development" stage. That usage will be understood herein unless the word "development" is otherwise qualified.

Douglas-fir in the past has generally required an intermediate culturing step between the advanced early stage embryo growth stage and the final cotyledonary embryo development stage. With this species many of the embryos form in tight clumps or clusters. These are first preferably singulated before going to the development stage. Singulation is carried out in a series of liquid shake cultures lacking auxins and cytokinins but which have exogenous abscisic acid added as a necessary new hormone. The level of osmotic potential is also reduced from that of the maintenance medium. ABA will usually initially be within the range of 5–15 mg/L (20–60 μM/L) with osmotic potential levels in the range of 130–160 mM/kg. Typically the singulation process will encompass two or three transfers at weekly intervals following the initial singulation treatment. A preferred procedure uses an initial treatment with ABA at a 10 mg/L level followed by two treatments at weekly intervals with ABA at a 5 mg/L concentration. Using the procedures of the present invention this singulation treatment may not always be necessary.

Further development and enlargement of the embryos will occur during the singulation stage for Douglas-fir. Maltose has again been found, very advantageous in place of sucrose as the carbon and energy source in Douglas-fir singulation media. Singulated embryos produced in maltose-containing media have larger heads and generally superior morphology to those produced when sucrose is employed. Some internal differentiation of cellular structure may begin to be seen in embryos at the end of the singulation stage.

The present invention should be considered sufficiently broad so that the terms "singulation" or "singulation stage" are fully equivalent to "maintenance culture" or "maintenance stage". The singulation stage may be considered a specialized type of maintenance stage.

In the case of Douglas-fir, if the embryos are not singulated many of them will later develop into a tight clump of cotyledonary embryos which cannot be readily separated and are difficult to use for further germination.

Significantly, species other than Douglas-fir can be advantageously cultured by beginning early cotyledonary embryo development in a series of media similar to those used for Douglas-fir singulation.

Whether or not the singulation stage has been employed, the advanced early stage embryos are then placed on a cotyledonary embryo development medium. For all species it is most desirable for the final development stage or stages to be carried out on either solid medium or with liquid medium using a pad system. For reasons not perfectly understood, far more vigorous embryos are normally obtained when they are exposed to air in the final development stages.

Especially when Douglas-fir is being cultured, but also with some genotypes of loblolly pine and other species, the osmotic potential of the later stage cotyledonary development medium should be sharply raised above that of any of the preceding media. Initially levels may be in the 300–350 mM/kg range but these should be increased to levels of at least about 400 mM/kg as development proceeds. If development is started at levels around 300–350 mM/kg, the osmotic level may be increased during development by a complete medium change, a partial change in which some old medium is replaced, or by adding an appropriate form, such as a solution, of osmoticants to the medium without replacement of any of the original medium. Any of these changes may be considered a transfer to a "new" medium. With Douglas-fir, it is preferred that the osmotic levels at the end of the development period should be at least about 450 mM/kg although with some genotypes lower levels are acceptable. With some Douglas-fir genotypes final osmotic levels as high as 600 mM/kg have given superior results. These higher levels tend to prevent deterioration and callusing of the embryos.

Osmotic potential in the later stages of cotyledonary development is best controlled by a combination of osmoticants. One of these should be a readily metabolized carbohydrate energy source, preferably a sugar such as sucrose, glucose, fructose, maltose, or galactose. Sucrose is a preferred ingredient and may be present in amounts in the range of 2–6%. The other is a poorly metabolized osmoticant of which sorbitol, lactose, or a polyalkylene glycol would be examples. In a solid development medium, a combination of sorbitol, lactose and polyethylene glycol has proved very effective. Polyethylene glycol (PEG) alone, in concentrations of about 15–30% of the medium, has worked very well in liquid development media. The molecular weight of the PEG is not critical and may fall in the range of several hundred to several thousand. While the salts and organic components of the medium make a small contribution to the osmolality, the osmotic potential is primarily controlled by the energy-providing sugar and the other osmoticants. It is sometimes advantageous to use one combination of osmoticants at the beginning of development and transfer to a medium having a different combination at some point during the development stage.

In some eases where transfers to fresh media are made during the cotyledonary embryo development stage, especially when culturing Douglas-fir, at least the final and most preferably the penultimate media should have osmotic potentials of at least about 350 mM/kg, preferably about 400 mM/kg or higher.

For virtually all coniferous species a supply of exogenous abscisic acid is usually an essential hormone and media component in the development from early stage embryos (FIGS. 1 and 2) to cotyledonary embryos (FIG. 3). As described in earlier U.S. Pat. Nos. 5,034,326 and 5,036,007, this was always used in combination with an adsorbent, such as activated charcoal. The adsorbent was present in a sufficient amount and form to slowly reduce the abscisic acid and remove metabolic waste products. It could not be present in such a high concentration as to deplete the abscisic acid in a very short time; e.g., in a matter of days. The combination of abscisic acid with the adsorbent usually required a higher initial concentration of abscisic acid than was the case if no adsorbent was present in the medium. Alternatively, ABA may be reduced in stepwise fashion as detailed in U.S. Pat. No. 5,236,841. Activated charcoal or other adsorbents are not necessary using the procedure of this patent. In the particular case of Douglas-fir, but with other species as well, I have found that the level of exogenous abscisic acid should be generally continuously lowered over time from the 5–15 mg/L normally found necessary at the beginning of the singulation step or cotyledonary embryo development stage to a level perhaps of about 1–2 mg/L, or even to zero, at the end of the development stage. Accurate measurements of abscisic acid present in the development stage have not yet been made due to the extreme difficulties of analyzing the medium. It is possible in some cases to produce cotyledonary embryos without exogenous ABA in the development medium. However, the embryos so produced are usually of inferior quality.

Following cotyledonary embryo development the embryos may be placed directly on a germination medium for conversion into plantlets (FIG. 4). Alternatively, they may be converted into artificial seeds by any of a number of published processes.

The germination medium has no exogenous hormones, a lowered organic nitrogen content, and a reduced level of osmoticants. After a sufficient time in darkness followed by light, or a 16 hour light and 8 hour dark photoperiod, the cotyledonary embryos will have developed into plantlets. Douglas-fir does not require an initial dark period although an initial four day dark period is usually more satisfactory. A one week dark period is useful for Norway spruce. The time period for germination will be about 1–2 months. The resulting plantlets will have a well developed radicle and cotyledonary structure with a growing epicotyl and are ready for planting in soil.

The present invention is primarily concerned with the composition of the embryo maintenance and multiplication media and the method of their use. In the case of Douglas-fir, the composition of the embryo singulation medium is also a concern. In particular, the replacement of sucrose by maltose as the carbon and energy source gives improved size and vigor of advanced early stage embryos and further improves the morphology of subsequently cultured cotyledonary embryos. This improvement is manifested in an improved conversion rate. Maltose has been found to be advantageous on concentrations as high as 6% w/v (60,000 mg/L) in the maintenance media. Preferred concentrations are on the 2–4% range.

It is an object of the present invention to produce coniferous plantlets by somatic embryogenesis.

It is another object to produce a large clone of a genetically selected forest species for reforestation using the methods of somatic embryogenesis and plant tissue culture.

It is a further object to provide a method of somatic embryogenesis that will dependably and consistently provide coniferous plantlets in large quantities.

It is yet another object to provide a method of somatic embryogenesis that can dependably and consistently reproduce large clones of selected individuals of forest species that heretofore have not been successfully reproduced by this method.

It is still a further object to provide a method whereby superior genotypes of coniferous trees can be multiplied by tissue culture in the large quantities needed for reforestation.

It is also an object to provide a method that will produce somatic embryos in large quantities with improved robust morphology for conversion into plantlets.

It is a particular object to provide a method and suitable culture media for somatic embryogenesis that produces robust somatic embryos with a high percentage of conversion to plants growing in soil.

It still another object to provide a method that generates more robust advanced early stage embryos of improved morphology and vigor.

These and many other objects will become readily apparent to those skilled in the art by reading the following detailed description, taken in conjunction with the drawings.

BRIEF DESCRIPTION OF THE DRAWINGS

The figures show various stages of plant embryogenesis in which.

DETAILED DESCRIPTION OF THE PREFERRED EMBODIMENTS

Figure 1:
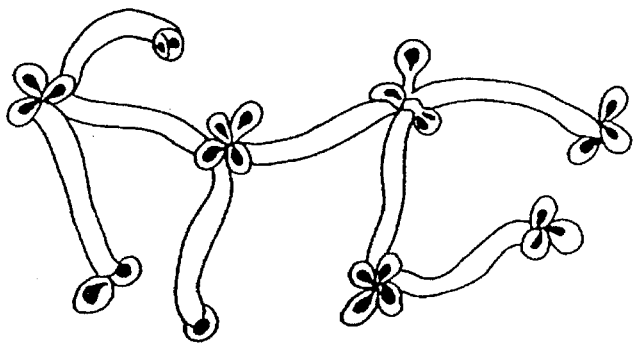
FIG. 1 shows early stage embryos.

The process of the present invention is not limited to any single basal culture medium or to the use of specific growth hormones other than those defined in the claims. Any of a number of well known basal media, such as that of Murashige and Skoog (1962), may be used. However, the present inventors have found the basal media described in Table 1 to give excellent results, particularly when used for culturing Douglas-fir (*Pseudotsuga menziesii*). The basal media are modified for each of the various culturing stages as shown in Table 2. Similar media particularly preferred for Norway spruce (*Picea abies*) are given in Tables 9 and 10, and for Loblolly pine (*Pinus taeda*) in Tables 11 and 12.

A number of abbreviations are used in the following text. These are in common use in the field of tissue culture.

BAP—$N^6$-benzylaminopurine (or $N^6$-benzyladenine), a cytokinin.

KIN—kinetin (6-furfurylaminopurine), also a cytokinin 2,4-D—2,4-dichlorophenoxyacetic acid, an auxin NAA—2-naphthylacetic acid (naphthalene-2-acetic acid), also an auxin.

ABA—abscisic acid (5-(1-hydroxy-2,6,6-trimethyl-4-oxo-2-cyclohexen-1-yl)-3-methyl-2,4-pentadienoic acid), a maturation promoter.

It will be understood by those skilled in the art that other plant growth hormones can be substituted for those just noted. As examples, IAA (indole-3-acetic acid), IBA (indole-3-butyric acid), and NAA (naphthalene-2-acetic add) are effective auxins and 2-IP ($N^6$-isopentenylaminopurine) and zeatin are frequently used as cytokinins.

As an aid in comparing the present work with other published data, the following table of conversions from weight to molar concentrations might be useful.

|  | 1 µM/L | 1 mg/L |
| --- | --- | --- |
| BAP | 0.225 mg/L | 4.44 µM/L |
| KIN | 0.215 | 4.65 |
| 2,4-D | 0.221 | 4.52 |
| NAA | 0.816 | 5.38 |
| ABA | 0.264 | 3.78 |

One of the parents of the present application, U.S. Pat. No. 4,957,866, pointed out the importance of the control of osmotic potential of the media used in the various culturing stages. A large group of chemical materials are suitable as osmoticants. In general these are highly water soluble polyhydroxylated molecules that include either simple or complex sugars, hexitols, and cyclitols. The cyclitols are normally six carbon ring compounds that are hexahydroxylated. The most readily available cyclitol is myo-inositol but any of the other eight stereoisomeric forms, such as scyllo-inositol are believed to be quite suitable. Among the sugars, sucrose and glucose are known to be very effective and have been widely used in the past.

Evaluation and quality ratings of early stage embryo quality in maintenance media is visual and subjective. However, a set of criteria have been developed for quality evaluation and different technicians trained in their use have given remarkably uniform ratings. The guidelines used for quality ratings in the examples that will follow are as follows:

| | |
| --- | --- |
| 0 | (a) all cells stressed — white stress spots on heads and/or suspensor cells.<br>(b) large cell masses.<br>(c) single cells only. |
| 1 | embryonic heads formed but rough or irregular. Suspensor cells partly organized around heads. |
| 2 | smooth embryonic heads with short suspensors partly organized around heads. |
| 3 | smooth organized embryos with well shaped heads and long suspensors. Heads still joined but beginning to singulate. Some singulated embryos present. |
| 4 | Well organized large embryos with smooth heads and long suspensor cells trailing. Most embryos single headed but a few joined ones may also be present. |

DOUGLAS FIR CULTURE

As noted in the background discussion of earlier U.S. Pat. No. 5,036,007, the embryogeny of Douglas-fir is quite different from trees such as the spruces or pines. One of these differences is seen when early stage embryos are placed in or on an advanced early stage embryo development medium. Instead of single advanced early stage embryos, Douglas-fir tends to develop tight clumps of these embryos. Upon further development into cotyledonary embryos, many of these clumps remain united and the resulting product is difficult to work with for further conversion. This phenomenon had apparently been recognized earlier by Durzan and Gupta (1987) who, while they did not discuss it specifically, transferred their embryonal-suspensor masses to a liquid shake culture containing 0.5 µM abscisic acid. They note that under the influence of ABA, individual bipolar embryos were produced which were then transferred to a development medium without ABA. The present method utilizes a series of liquid shake cultures with reduced osmotic level and added abscisic acid between the advanced early stage embryo development and cotyledonary embryo development stages to achieve the necessary singulation. Osmotic level is again raised to levels generally above about 450 mM/kg during the final cotyledonary embryo development stage or stages.

A basal culture medium has been developed by the present inventors specifically to give more successful initiation and multiplication of Douglas-fir. Preferred media compositions are given in Tables 1 and 2. A number of ingredients may be varied in quantity, such as those that affect the level and balance between organic and inorganic nitrogen, depending on the response of individual genotypes. This response cannot be readily predicted and media optimization must largely be achieved by a combination of intuition and trial and error.

Sorbitol (D-glucitol), D-mannitol, and galactitol (dulcitol) are straight chain sugar alcohols suitable as osmoticants. Lactose is a sugar effective as an osmoticant. Other materials suitable as osmoticants may include glycol ethers such as poly(ethylene glycol) and poly(propylene glycol) and their respective monomers.

While inorganic salts and pure simple organic chemicals generally behave similarly in culture media regardless of supplier, there are occasions when this is not the case for the more complex materials. Without intending endorsement of any product over available alternatives, chemicals from the following suppliers were used throughout the experiments to be described in the examples. Agar was obtained from Difco Laboratories, Detroit Mic. Where specified as "tissue culture agar" the supplier was Hazleton Biologics, Inc., Lenexa, Kans. Casamino acids, a casein hydrolysate, was also supplied by Difco Laboratories. Activated charcoal was obtained from Sigma Chemical Company, St. Louis Mo., as their grade NUC-4386.

TABLE 1

Pseudotsuga Menziesii Basal Culture Media

| Constituent | Concentration, mg/L | |
|---|---|---|
| | WTC[1] | BM$_G$[2] |
| BASAL SALTS | | |
| NH$_4$NO$_3$ | — | 206.3 |
| KNO$_3$ | varies[1] | 1170.0 |
| CaCl$_2$.6H$_2$O | 200.0 | 220.0 |
| Ca(NO$_3$)$_2$.4H$_2$O | varies[1] | — |
| KH$_2$PO$_4$ | 340.0 | 85.0 |
| MgSO$_4$.7H$_2$O | 400.0 | 185.0 |
| MnSO$_4$.H$_2$O | 20.8 | 8.45 |
| ZnSO$_4$.7H$_2$O | 8.0 | 4.30 |
| CuSO$_4$.5H$_2$O | 0.024 | 0.013 |
| FeSO$_4$.7H$_2$O | 27.85 | 13.93 |
| Na$_2$EDTA | 37.25 | 18.63 |
| H$_3$BO$_3$ | 5.0 | 3.10 |
| NaMoO$_4$.2H$_2$O | 0.20 | 0.125 |
| CoCl$_2$.6H$_2$O | 0.025 | 0.0125 |
| KI | 1.00 | 0.42 |
| ORGANIC ADDITIVES | | |
| myo-Inositol | varies[1] | 100.0 |
| Thiamine.HCl | 1.00 | 1.00 |
| Nicotinic acid | 0.50 | 0.50 |
| Pyridoxine.HCl | 0.50 | 0.50 |
| Glycine | 2.00 | 2.00 |
| L-Glutamine | varies | 450.0 |
| Casamino acids | 500.0 | — |
| Sugar as specified | varies | 20,000. |
| pH | 5.7 | 5.7 |

[1]Usage varies according to culturing stage and genotype.
[2]Modified Gupta and Durzan medium BM$_3$ (1986). Medium BM$_G$ of U.S. Pat. No. 5,034,326.

In Table 2 sucrose is the sugar used in Stage 1 and Stages 5 and 6. In Stages II, III, and IV sucrose or maltose is used as shown in the specific examples. Maltose has proved to give superior results.

It will be seen by reference to the media compositions that the features of the earlier inventions described in the patents already noted are advantageously used at present with Douglas-fir. A raised osmotic level following initiation is desirable for good quality advanced early stage embryo development. This level will differ somewhat between genotypes within each species as it does between species. Similarly, the level of abscisic acid present should be gradually reduced during the singulation stage and also during the cotyledonary embryo development period, if exogenous ABA is added in that stage. This may be done either by the inclusion of activated charcoal in the medium or by a stepwise reduction effected by multiple transfers to media of successively lower ABA concentration. The exogenous ABA level is preferably gradually reduced from that present at the beginning of the singulation stage so that little or none is available at the end of the development period.

The examples that follow represent the best mode known at present for culturing Douglas-fir by somatic embryogenesis. While the later examples are principally directed to the maintenance and singulation stages, the steps prior to that time and following will first be briefly outlined in the following example.

EXAMPLE 1

A preferred explant for Douglas-fir is an immature zygotic embryo with the gametophyte still attached. Best results have been realized with embryos selected in the interval just prior to the development of an apical dome up to the time just before cotyledon primordia become visible. The cones are split longitudinally and seeds isolated from young ovuliferous scales. Seeds are sterilized by first being agitated in 10% Liqui-Nox laboratory cleaner (Alconox, Inc, New York, N.Y.) with a small additional amount of liquid surfactant for about 10 minutes. They are then rinsed in running tap water for 30 minutes. At this time they are transferred to a sterile hood and agitated in 20% H$_2$O$_2$ for 10 minutes.

TABLE 2

| | Stage I Initiation | Stage II Maintenance 1 | Stage III Maintenance 2 | Stage IV Singulation | Stage V Development | Stage VI Germination |
|---|---|---|---|---|---|---|
| Basal Medium | WTC | WTC | WTC | WTC | WTC | BM$_G$ |
| KNO$_3$ | 1250[1] | 1250–2500 | 1250 | 1050 | 1000–2500 | 1170 |
| Ca(NO$_3$)$_2$.4H$_2$O | — | — | — | 200 | — | — |
| myo-Inositol | 1000 | 5,000–10,000 | 5,000–10,000 | 100 | 100 | 100 |
| L-Glutamine | 450 | 450 | 1000 | 1000 | 750–1500 | — |
| Amino acid mixture[2] | — | — | — | — | 290 | — |
| Sugar | 15,000 | 30,000 | 30,000 | 20,000 | 20,000–60,000 | 20,000 |
| Supp. carbohydrate | — | — | — | — | 30,000–300,000 | — |
| 2,4-D | 110 | 1.1 | 1.1 | — | — | — |
| N$^6$-Benzyladenine | 45 | 0.22 | 0.22 | — | — | — |
| Kinetin | 43 | 0.22 | 0.22 | — | — | — |
| Abscisic acid | — | — | — | 5–15 | 0–50 | — |
| Gibberellins GA$_n$ | — | — | — | 0–15 | 0.5–25 | — |
| Activated charcoal | 2500 | — | — | — | 0–2500 | 2500 |
| Agar | 5000 | 5000 | — | — | — | 8000[4] |
| Gelrite | — | — | — | — | 3000[3] | — |

[1]All units are in mg/L (or ppm).
[2]L-Proline — 100, L-Asparagine — 100, L-Arginine — 50, L-Alanine — 20, L-Serine — 20.
[3]Not used for liquid media.
[4]Tissue culture agar.
The pH of all media are adjusted to 5.7.

Following five rinses in sterile deionized water the seed coat is split and the female gametophyte removed. This is split on one side and the embryo teased out while still remaining attached to the gametophyte by the suspensor. An explant so prepared is placed on the Stage I solid initiation medium in a 50 mm petri dish. The explants are incubated in the dark from 4–8 weeks. Success in forming an embryonal-suspensor mass (ESM) containing early stage embryos varies from about 1–10% depending on a number of variable factors which presently are not well understood. Sucrose is the preferred sugar used in the initiation medium.

All stages of culture are carried out at temperatures which may vary between about 20°–25° C. Temperature is not generally critical and may, on occasion be varied so as to fall outside this range.

The embryonal-suspensor masses containing early stage embryos are transferred to a solid Stage II maintenance and multiplication medium containing greatly reduced plant growth hormones and a raised osmotic level. Again, culturing is carried out in the dark with subcultures made at no greater than about two week intervals. The clone can be maintained at this stage for long periods of time. In both the solid Stage II and the following Stage III liquid maintenance media maltose is substituted for the sucrose used in the initiation culture on an equal weight basis unless otherwise indicated in the following examples.

Early stage embryos from the Stage II multiplication step are then transferred to a liquid Stage III second maintenance medium having an osmotic level generally the same as that of the Stage II medium. An osmotic level of at least about 170 mM/kg will usually suffice for Douglas-fir although some genotypes may require levels as high as 240 mM/kg. Myo-inositol, which will normally be around 5000 mg/L, may need to be adjusted somewhat depending on the needs of the particular genotype in order to obtain optimum results. Culture is carried out in the dark and is periodically subcultured, usually weekly. Robust advanced early stage embryos estimated to have 100 or more cells will develop during this time, normally 5–6 weeks.

Following advanced early stage embryo development in Stage III, the cultures are transferred to a Stage IV liquid medium for the singulation step referred to earlier. Again, in this medium it has been found very beneficial to use maltose in preference to sucrose as the carbon and energy source. The singulation medium has a reduced osmotic level and is free of auxins and cytokinins. Abscisic acid is a newly added hormone in an initial amount in the range of about 5–15 mg/L, more usually about 5–10 mg/L. Cultures are again carried out in the dark. From two to four subcultures are made on a weekly basis. The level of exogenous abscisic acid will drop somewhat during each subculture. It is generally preferred that the level of abscisic acid at the beginning of a new subculture should not be significantly higher than the level used in the previous subculture. A preferred schedule is one week on a medium containing 10 mg/L ABA, a second week on a medium containing 5 mg/L ABA, and a third week on a medium also with 5 mg/L ABA. This gradual decrease in ABA level will continue through the development period.

After the final singulation treatment the embryos are rinsed with a fresh singulation medium in which ABA is reduced to 2.5 mg/L, before transfer to the cotyledonary development medium.

Following the singulation period the embryos are ready to complete their development to cotyledonary embryos on a Stage V medium. They are transferred to either a solid medium or supported on a pad or bridge of filter paper using a liquid medium. This will normally contain exogenous ABA which may be present up to about 50 mg/L. More typically, ABA will not generally exceed about 10 mg/L and most usually will not initially exceed 5 mg/L and may be considerably lower. In some cases it is not necessary to add any exogenous ABA to the development medium since a sufficient amount will be carried over with the residual singulation or rinse medium accompanying the embryos when the transfer is made from the last singulation stage. The development medium may also contain from 0.5–50 mg/L of a selected gibberellin. This is preferably $GA_{4/7}$. $GA_3$ is also useful although it is somewhat less effective in most cases. Other active gibberellins would also be expected to be beneficial at this stage. In cases where an adsorbent such as activated charcoal is not used in the development medium concentrations of GA and ABA will be significantly lower than the maximum levels just noted; e.g., by a full order of magnitude.

It has been found preferable for Douglas-fir to carry out development cultures entirely in the dark. Activated charcoal is preferably used in the development medium to effect ABA reduction over time but it is not essential. Particularly for Douglas-fir, a raised osmotic level in the development medium is very highly desirable. Osmotic levels should be above about 400 mM/kg and for some genotypes may advantageously be considerably higher. The effect of osmotic level is discussed in detail in U.S. Pat. No. 5,036,007.

Following the development stage the cotyledonary embryos may be placed on a Stage VI germination medium for production of plantlets. Alternatively, they may be placed in artificial seeds for sowing in soil or other medium.

EXAMPLE 2

An experiment was carried out using cultures of three Douglas-fir genotypes with four different maintenance media. These were made using 3% and 5% sucrose and 3% and 5% maltose. These concentrations of sugars were used in both the Stage II and Stage III maintenance media. Cultures were replicated three times. The first cultures in the Stage III liquid media were made using the entire culture of embryonic cells from the Stage II solid media using 20–25 mL of medium in a 250 mL Erlenmeyer flask. Thereafter subcultures were made using 5 mL settled cells and 45 mL of medium. Four to five subcultures were made on a weekly basis. Quality rating of the advanced early stage embryos is shown in Table 3.

TABLE 3

| Media/Genotype | 735 | 995/36 | 923/2 |
|---|---|---|---|
| 3% Sucrose | 1 | 1½ | 2 |
| 3% Maltose | 1½ | 2 | 2½ |
| 5% Sucrose | ½ | 1 | 1½ |
| 5% Maltose | 0 | 0 | 0 |

It is evident that 3% maltose improved embryo quality as compared with 3% or 5% sucrose in all cases. Under the conditions employed in this particular experiment 5% maltose appears to be toxic to the embryos. The reason for this is not known. As will be seen in the following example, as much as 5% maltose was readily tolerated although this appears to be near the upper limit. In addition to improved embryo quality, the number of embryos was also noticeably increased although no quantitative estimate was made.

EXAMPLE 3

The above experiment was repeated using Genotype 995/36 from the previous example and three new genotypes of Douglas-fir. Embryo quality was observed as follows after 4–5 Stage III subcultures:

TABLE 4

| Media/Genotype | 711 | 925/2 | 732 | 979/169 |
|---|---|---|---|---|
| 3% Sucrose | 1½ | 1 | 1¾ | 2 |
| 3% Maltose | 2½ | 2 | 3 | 3 |
| 5% Sucrose | 1½* | 1* | 1* | 2* |
| 5% Maltose | 2 | 1½ | 2 | 2½ |

*Stress spots present on embryo heads.

The improved embryo quality resulting from the use of maltose in the maintenance medium is again readily apparent. In the present experiment both 3% and 5% maltose were superior to either of the sucrose containing media. The results using a medium with 3% maltose were superior to the medium using 5% maltose.

Average osmolalities of the media containing sucrose were noted to increase after each one week culture period. The medium with 3% sucrose increased from 190 to 260 mM/kg while that with 5% sucrose went from 300 to 359 mM/kg. The 3% maltose medium showed only an insignificant change from an initial 189 to 193 mM/kg while the 5% maltose medium increased from 260 to 261 mM/kg.

EXAMPLE 4

To further investigate the effect of osmotic change during the weekly subculturing periods, in this example 3% filter sterilized maltose was used in side-by-side comparison with the 3% sucrose normally used in the Stage II and III Douglas-fir maintenance media. The Stage 3 liquid shake culture was carried out using 270 mL of medium and 30 mL of settled cells in 1 L Erlenmeyer flasks.

Figure 5:
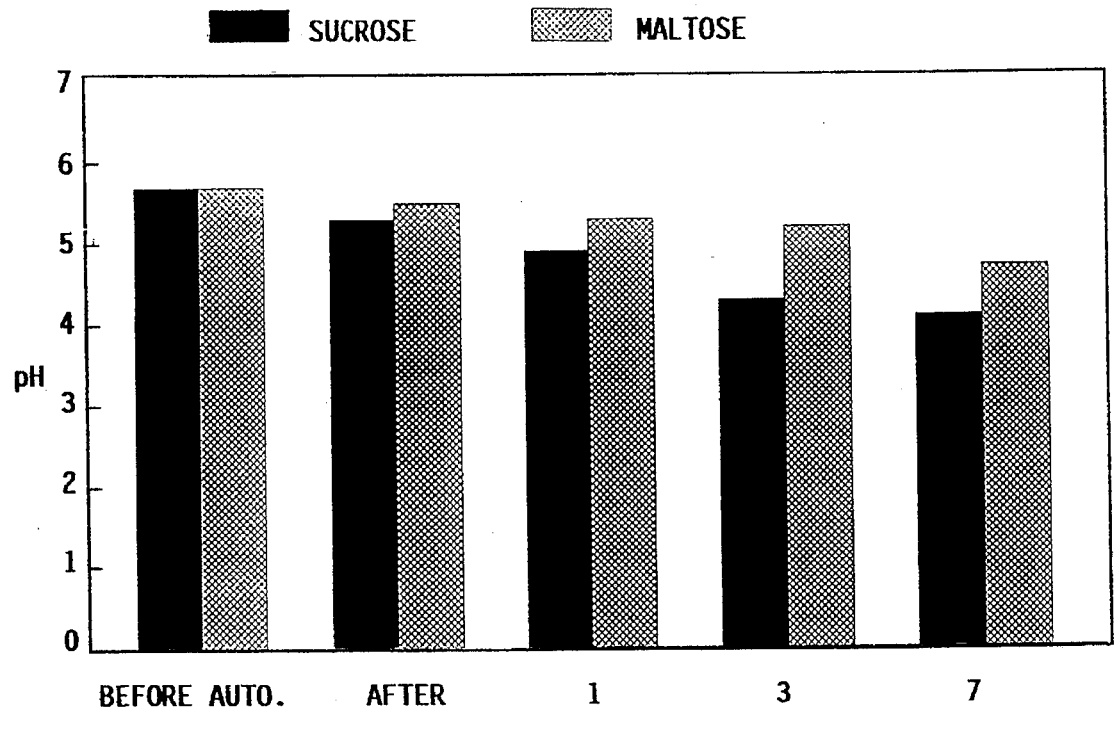
FIGS. 5 and 6 respectively show changes over time in pH and osmolality of maintenance media made using sucrose and maltose.
Figure 6:
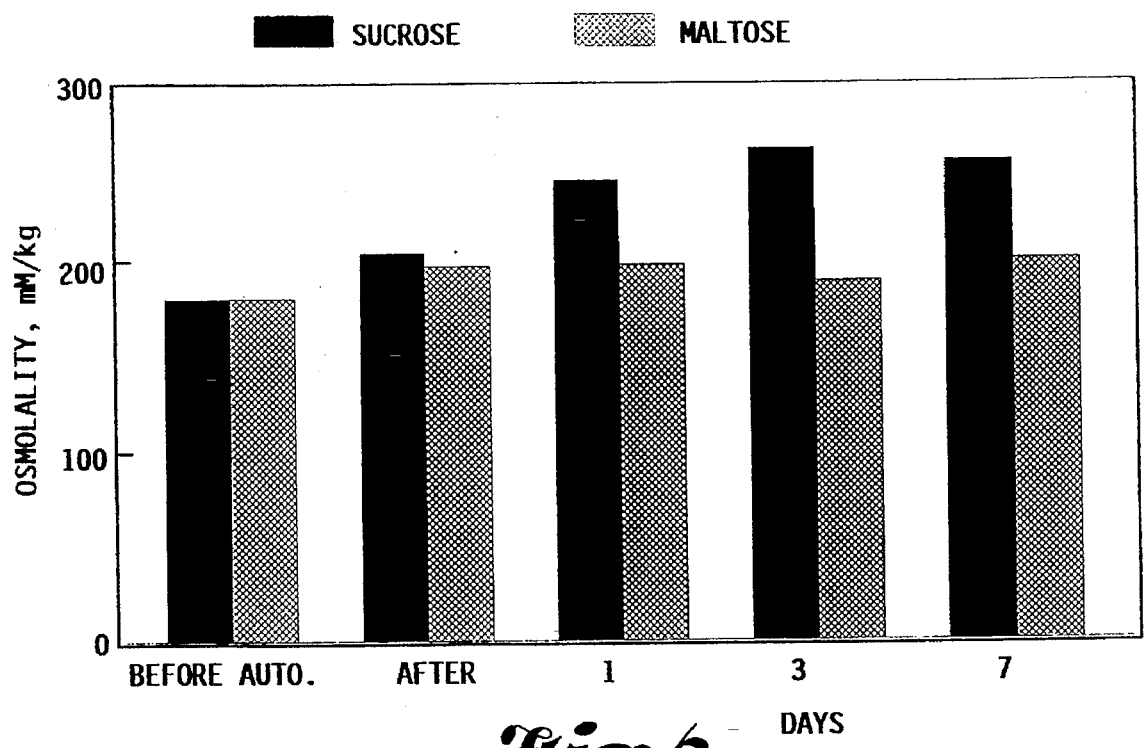

Three replicate treatments were carried out for each of eight genotypes, a total of 48 cultures. Readings were taken of pH and osmolality of a sampling of the media before and after autoclaving and after 1, 3, and 7 days of culturing. Results are averaged shown on the bar graphs of FIGS. 5 and 6 and given in more detail in Table 6. Both sucrose and maltose experienced a drop in pH over the period but this was far more marked in the case of sucrose. The sucrose media showed a very significant rise in osmolality over the period while the maltose media were essentially unchanged. Embryo quality ratings for seven genotypes are listed below in Table 5.

TABLE 5

| Genotype/Sugar | Sucrose | Maltose |
|---|---|---|
| 955/9 | 1½ | 2½ |
| 905/4 | 1 | 1¾ |
| 924/4 | 1½ | 3 |
| 948/14 | 1¼ | 2½ |
| 924/2 | ¾ | 1¼ |
| 954/14 | ¾ | 1¼ |
| 980/14 | 1 | 1¾ |

TABLE 6

| | | Sucrose | Maltose |
|---|---|---|---|
| Before Autoclaving | pH | 5.7 | 5.7 |
| | Osmolality | | |
| After Autoclaving | pH | 5.31 | 5.5 |
| | Osmolality | 201 | 198 |
| After 3 Days Geno. 980/14 | pH | 4.3 | 5.2 |
| | Osmolality | 260 | 189 |
| Geno. 989/46 | pH | 4.5 | 5.16 |
| | Osmolality | 228 | 190 |
| Geno. 924/4 | pH | 4.3 | 4.6 |
| | Osmolality | 230 | 190 |
| After 7 days Geno. 980/14 | pH | 4.2 | 4.7 |
| | Osmolality | 252 | 200 |
| Geno. 989/46 | pH | 4.12 | 4.68 |
| | Osmolality | 260 | 200 |
| Geno. 924/4 | pH | 4.2 | 4.7 |
| | Osmolality | 259 | 203 |

It appears that sucrose hydrolyzes into its component simple sugars, glucose and fructose, very early in the culturing stage to cause the osmolality increase. Maltose appears to be much more stable in this regard. This increase in osmolality of the sucrose media above an optimum level may be detrimental to embryo quality. An alternative explanation may be that fructose, a hydrolysis product of sucrose, may be toxic or is otherwise a poorly metabolized or inefficient energy source.

Figure 7:
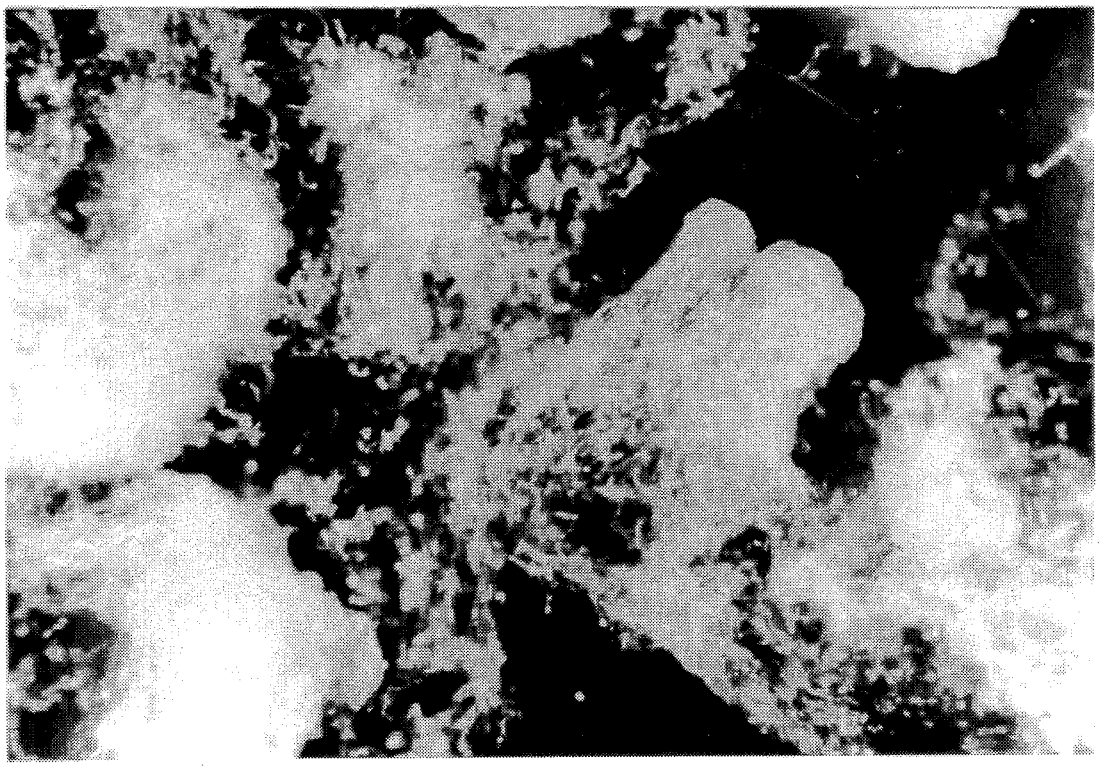
FIGS. 7 and 8 are microphotographs showing early stage and advanced early stage Douglas-fir embryos maintained respectively on sucrose and maltose-containing media.
Figure 8:
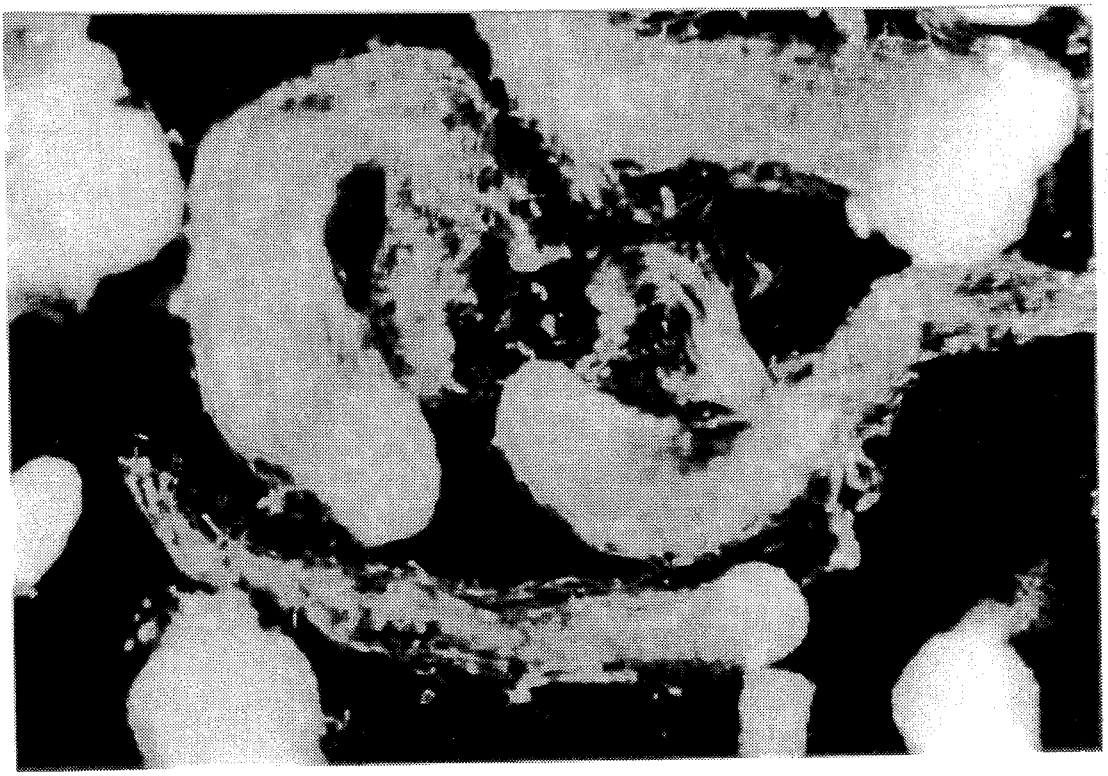

For all genotypes the advanced early stage embryo quality was signifcantly improved using maltose. FIGS. 7 and 8 show typical embryos. These are photomicrographs at 2.5× in which FIG. 7 is representative of the early stage embryos cultured on the sucrose-containing medium and FIG. 8 representative of the embryos cultured on maltose-containing medium. The improved head size and morphology of the maltose treated embryos shown in. FIG. 8 is immediately evident.

EXAMPLE 5

In this experiment 3% sucrose, 3%, 3.5%, and 4% maltose, 2% glucose, 2% fructose, and a mixture of 1% glucose and 1% fructose were compared as energy sources in the Stage 3 liquid maintenance medium for Douglas-fir culture. In all of these cultures sucrose was used as the sugar in the Stage II medium. No subcultures were made at Stage II and the cultures were transferred to Stage III after two weeks. Four genotypes were used with each condition being replicated three times. Subcultures were carried out in 250 mL Erlenmeyer flasks using 5 mL of settled cells and 45 mL of the medium being tested. Embryo quality measurements after 4–5 subcultures are given in Table 7.

TABLE 7

| Medium/Genotype | 948/20 | 711 | 732 | 979/169 |
|---|---|---|---|---|
| 3% Sucrose | 2 | 1½ | 1½ | 1 |
| 3% Maltose | 3 | 2 | 2½ | 1½ |
| 3.5% Maltose | 3¼ | 2 | 2¼ | 1¾ |
| 4% Maltose | 3 | 1¾ | 2 | 2 |
| 2% Glucose | 2 | 1½ | 1¾ | 1¼ |
| 2% Fructose | 1½* | 1* | 1½* | 1* |
| 1% Glucose + 1% Fructose | 1 | 1¼ | 1½ | 1 |

*Virtually all embryos had stress spots on the heads.

It is readily apparent that embryo quality from the 3% and 4% maltose containing media was superior to those grown on any of the other media. The use of 2% fructose gave embryos of decidedly inferior quality while those using the glucose/fructose mixture were generally poorer than those grown on the sucrose medium. These results suggest that the fructose produced by hydrolysis of sucrose may be the major detrimental factor to embryo quality rather than the osmotic rise observed with the sucrose containing media.

EXAMPLE 6

It was noted earlier that maltose was beneficial when used as the carbon and energy source for the Stage IV Douglas-fir singulation cultures following the maintenance stages. The following experiment was designed to show this effect. Two batches of Stage IV singulation medium (from Table 2) was made up, one using 2% sucrose and the other 2% maltose. The singulation treatment was started using 5 mL of settled cells from Stage III and 45 mL of medium in 250 mL Erlenmeyer flasks. A singlation schedule of 10/5/5 mg/L ABA was used. The initial singulation medium contained 10 mg/L ABA. After one week the embryos were transferred to a medium of similar composition except that ABA was reduced to 5 mg/L. Again, after a week in the second medium the embryos were transferred to a third medium identical to the second one; i.e., with 5 mg/L ABA, for a third week of treatment. Following the singulation treatment the embryos were rinsed with the Stage IV shake medium having 2.5 mg/L ABA prior to transfer to a Stage V cotyledonary development medium Three genotypes of Douglas-fir were used in the present experiment. Table 7 shows embryo quality ratings after the first and second ABA shake treatments.

TABLE 8

| Genotype/Sugar | ABA 10 mg/L | | ABA 5 mg/L | |
| --- | --- | --- | --- | --- |
| | Sucrose | Maltose | Sucrose | Maltose |
| 711 | 2½ | 2 | 2¼ | 3 |
| 995/36 | 2¼ | 2½ | 2¼ | 3 |
| 732 | 1¾ | 2 | 1¾ | 2 |

Ratings similar to the above were not made after the third singulation stage. However, photographs were made at that time of all three genotypes. It is evident from these that the embryos from the maltose containing media all had larger and smoother heads and that better singulation had occurred. Genotypes 711 and 732 also had longer suspensors, although this was not observed with genotype 995/36. Similar significant improvements were also observed with other genotypes.

EXAMPLE 7

Advanced early stage embryos from the last singulation stage were rinsed as noted above and 1 mL was plated on Stage V using polyester pads saturated with 10 mL of cotyledonary development medium. Three prior embryo treatments prior to plating on the development media were compared. One treatment had employed sucrose in both Stage II and Stage III maintenance stages and in the Stage IV singulation stage. Another had used maltose in the two maintenance stages but sucrose in the singulation treatments. The third had used maltose in both maintenance stages and also in the singulation stage. In this trial the development medium was made using sucrose. After a 5–6 weeks culturing period the resulting cotyledonary embryos were evaluated. Those grown on the maltose maintenance medium but with the sucrose singulation media were more elongated with less callusing at the radicle end than those cultured on only sucrose media. In addition, the yield was markedly higher with those on the maltose media averaging 45 ±7 compared with 23 ±6 embryos per plate on the all sucrose media. Cotyledonary embryos grown on both maltose containing maintenance and singulation were elongated even more with a yield per plate of 42 ±5 embryos per plate. Morphology of cotyledonary embryos grown on either maltose regimen was markedly more like zygotic embryos than those on the sucrose regimen. They tended to be more evenly tapered and smoother, with far fewer wart-like protuberances or callusing on the surface.

In view of the teachings of U.S. Pat. No. 5,187,092 it would be expected that a cotyledonary embryo development medium in which sucrose was replaced in whole or in part with maltose or glucose would be advantageous. Surprisingly, this has not been found to be the case with all genotypes of Douglas-fir or with the other species reported in the following examples. In fact, when sucrose was replaced with maltose in the Stage V medium two of the Douglas-fir genotypes cultured showed markedly poorer embryo quality. The reasons for this are not well understood but may relate to the higher osmotic environment in the present development media compared with that in the patent, or it may be species dependent. The use of maltose at the earlier stages of embryo development appears to be considerably more important than its use in embryo maturation.

EXAMPLE 8

Surprisingly, it has been found that a maltose containing medium need not be used throughout the entire maintenance period. Two or three weekly subcultures in a liquid maltose medium following maintenance in a conventional sucrose containing medium will normally suffice. In the case of Douglas-fir this will usually also serve to provide adequate singulation without the necessity of a separate singulation step.

The term "maintenance" should be considered here to include both subculturing on hormone free maintenance medium or on growth hormone containing "maintenance and multiplication" media.

This subsequent maltose-based maintenance treatment, as it might be called, is most preferably done without the use of growth hormones in the medium. While the inclusion of the usual amounts of auxins and/or auxins and cytokinins is permissible, significantly better results will be achieved if they are omitted entirely. Omission of the hormones is particularly desirable if good singulation of Douglas-fir is to be achieved.

In the following experiments three genotypes of Douglas-fir were subjected to four treatments following a conventional maintenance and multiplication treatment using a sucrose containing medium (See Table 2, Stage III, Maintenance). Each treatment consisted of three weekly subcultures. The first used the unchanged 3% sucrose maintenance medium with 1.1 mg/L of 2,4-D and 0.22 mg/L each of BA and kinetin. The second was similar except that 3% maltose was substituted for sucrose. The third medium contained 3% maltose but had no BA or kinetin, only the 2,4-D was retained. In the fourth treatment 3% maltose was used without any growth hormones. Embryo head size (length in mm) was measured as an indication of quality using a randomly selected sample of 10 embryos from each culture for each genotype. All embryos were still in precotyledonary advanced early stage form. Results are seen in Table 9.

TABLE 9

Embryo Head Length, mm

| Genotype | Sucrose with all Hormones | Maltose with all Hormones | Maltose with only 2,4-D | Maltose with no Hormones |
|---|---|---|---|---|
| 905.4 | 0.031 | 0.092 | 0.116 | 0.152 |
| 948.14 | 0.093 | 0.144 | 0.179 | 0.21 |
| 924.4 | 0.101 | 0.194 | 0.218 | 0.255 |

An analysis of variance using the entire data set showed differences between treatments to be significant at or above the 95% level. Clear improvements are seen as hormones are selectively eliminated. Embryo head morphology was particularly improved in the treatment lacking hormones.

Embryos from each of the treatments were then plated on cotyledonary embryo development medium (see Table 2, Stage V) containing 6% sucrose as the carbohydrate source. This medium was in liquid form absorbed in fibrous pads and 1 mL of settled advanced early stage embryos were placed directly on the surface of the liquid saturated pad. Results, shown in Table 10, are average counts of four plates.

TABLE 10

Average Cotyledonary Embryo Yields with Different Maltose Treatments

| Genotype | Sucrose with all Hormones | Maltose with all Hormones | Maltose with only 2,4-D | Maltose with no Hormones |
|---|---|---|---|---|
| 905.4 | 0 | 1 | 3.8 | 19.8 |
| 948.14 | 1 | 3.8 | 6.8 | 9.8 |
| 924.4 | 0 | 1 | 3.5 | 6 |

Again, analysis of variance showed highly significant differences between the different treatments studied which immediately followed a maintenance and multiplication stage using sucrose. One exception was the sucrose treatment and the maltose treatment which had the full hormone regimen and these were not statistically different. It is readily apparent that brief maintenance on the maltose medium with only 2,4-D, or preferably with no hormones at all, is highly advantageous in terms of cotyledonary embryo yield.

NORWAY SPRUCE CULTURE

While the media compositions and growth hormone usages described in the previous examples of this application are those presently regarded as optimum for Douglas-fir, different concentrations and mixtures appear more suitable for other species. The following tables show preferred media for culture of Norway Spruce by somatic embryogenesis.

TABLE 11

Picea Abies Basal Culture Media

| | Concentration, mg/L | |
|---|---|---|
| Constituent | A[1] | B[2] |
| BASAL SALTS | | |
| $NH_4NO_3$ | — | 206.3 |
| KCl | 372.5 | — |
| $KNO_3$ | 50.0 | 2340.0 |
| $KH_2PO_4$ | 85.0 | 85.0 |
| $MgSO_4.7H_2O$ | 160.0 | 185.0 |
| $CaCl_2.6H_2O$ | 220.0 | 220.0 |
| KI | 0.415 | 0.415 |
| $H_3BO_3$ | 3.10 | 3.10 |
| $MnSO_4.H_2O$ | 8.45 | 8.45 |
| $ZnSO_4.7H_2O$ | 4.30 | 4.30 |
| $NaMoO_4.2H_2O$ | 0.125 | 0.125 |
| $CuSO_4.5H_2O$ | 0.0125 | 0.0125 |
| $CoCl_2.6H_2O$ | 0.0125 | 0.0125 |
| $FeSO_4.7H_2O$ | 13.90 | 13.93 |
| $Na_2EDTA$ | 18.65 | 18.63 |
| ORGANIC ADDITIVES | | |
| Sucrose | 10,000. | 30,000. |
| myo-Inositol | 50.0 | 1000.0 |
| Casamino acids | — | 500.0 |
| L-Glutamine | 750.0 | 450.0 |
| Thiamine.HCl | 0.05 | 1.00 |
| Pyridoxine.HCl | 0.05 | 0.50 |
| Nicotinic acid | 0.25 | 0.50 |
| Glycine | — | 2.00 |
| L-Asparagine | 50.0 | — |
| pH | 5.8 | 5.7 |

[1] Institute of Paper Chemistry medium (Verhagen and Wann 1989)
[2] Gupta and Durzan medium $BM_3$ (1986).

Table 12

Composition of *Picea Abies* Media for Different Stage Treatments $BM_1$—Induction Medium
$BM_A^{(1)}$+NAA$^{(3)}$(10.8 µM)+BAP$^{(4)}$ (4.41 µM)+7.0 g/L Difco agar.
[1] Basal medium A from Table 9
[3] 2-Naphthylacetic acid (Naphthalene-2-acetic acid)
[4] $N^6$-Benzylaminopurine $BM_M$—Maintenance and Multiplication Medium
$BM_B^{(2)}$+2,4-D$^{(5)}$ (5 µM)+BAP (2 µM)+KIN$^{(6)}$ (2 µM). 6.0 g/L Difco agar added if solid medium is desired. Maltose is substituted for sucrose as shown in specific examples.
[2] Basic medium B from Table 9
[5] 2,4-Dichlorophenoxyacetic acid
[6] Kinetin $BM_D$—Cotyledonary Embryo Development Medium
$BM_B$+40.0 mg/L Arginine+100 mg/L Asparagine+6.0 g/L Tissue Culture Agar+Abscisic acid (as specified)+Activated charcoal 1.25 g/L. $KNO_3$ is reduced to 1170 mg/L in basal salts.

$BM_G$—Germination Medium
$BM_B$ with $KNO_3$ reduced to 1170 mg/L, myo-Inositol reduced to 100 mg/L, Sucrose reduced to 20.0 g/L, and L-Glutamine and Casamino acids removed. 2.5 g/L of Adsorbent and 6.0 g/L of Tissue Culture Agar are added.

Initiated cultures of Norway Spruce embryonal-suspensor mass containing early stage embryos were placed first on solid $BM_M$ maintenance media containing 3% sucrose, 1.5% sucrose+1.5% maltose, and 3% maltose. The embryos were then transferred to the liquid maintenance medium and subcultured weekly for 5–6 weeks. Results were similar to those just reported for Douglas-fir. The advanced early stage embryos maintained on the 3% maltose medium were larger, smoother, and generally superior in morphology and vigor than those held in either of the other cultures.

LOBLOLLY PINE CULTURE

The following schedule of treatments has been very successfully used for the growth of plantlets by somatic embryogenesis of loblolly pine (*Pinus taeda*). Explants were the female gametophytes containing the zygotic embryos which had been removed from seeds 4 to 5 weeks after fertilization. The seed coat was removed but the embryo was not further dissected out of the surrounding gametophyte other than to excise the nucellar end. Seeds were obtained from cones supplied by a Weyerhaeuser Company seed orchard located at Washington, N.C. The cones were stored at 4° C. until used. Immediately before removal of the immature embryos the seeds were sterilized using a modified method of Gupta and Durzan (1985). Briefly, this involves an initial washing and detergent treatment followed by a first sterilization in 30% $H_2O_2$ and a second in diluted 10% v/v household bleach. The additional $HgCl_2$ treatment used by Gupta and Durzan was not found to be necessary to ensure sterility. The explants were thoroughly washed with sterile distilled water after each treatment.

Tables 13 and 14 give media compositions for loblolly pine embryogenesis.

TABLE 13

*Pinus Taeda* Basal Medium (Modified 1/2 P6 Basal Salts*)

| Constituent | Concentration, mg/L |
|---|---|
| $NH_4NO_3$ | 150.0 |
| $KNO_3$ | 909.9 |
| $KH_2PO_4$ | 136.1 |
| $Ca(NO_3)_2.4H_2O$ | 236.2 |
| $CaCl_2.4H_2O$ | 50.0 |
| $MgSO_4.7H_2O$ | 246.5 |
| $Mg(NO_3)_2.6H_2O$ | 256.5 |
| $MgCl_2.6H_2O$ | 50.0 |
| KI | 4.15 |
| $H_3BO_3$ | 15.5 |
| $MnSO_4.H_2O$ | 10.5 |
| $ZnSO_4.7H_2O$ | 14.4 |
| $NaMoO_4.2H_2O$ | 0.125 |
| $CuSO_4.5H_2O$ | 0.125 |
| $CoCl_2.6H_2O$ | 0.125 |
| $FeSO_4.7H_2O$ | 13.9 |
| $Na_2EDTA$ | 18.65 |
| Sucrose | 30,000. |
| myo-Inositol | 100. |
| Casamino acids | 500.0 |
| L-Glutamine | 1000.0 |
| Thiamine.HCl | 1.00 |
| Pyridoxine.HCl | 0.50 |
| Nicotinic acid | 0.50 |
| Glycine | 2.00 |
| Agar+ | 6,000. |
| pH adjusted to 5.7 | |

*According to Teasdale, Dawson, and Woolhouse (1986) as modified
+Used if a solid medium is desired

Table 14

Composition of Media for Different Stage Treatments

BM₁—Induction Medium

BM+2,4-D (50 μM)+KIN (20 μM)+BAP (20 μM)

BM₂—Maintenance and Multiplication Medium

BM+2,4-D (5 μM)+KIN (2 μM)+BAP (2 μM)+4900 mg/L additional myo-inositol. Maltose is substituted for sucrose on an equal weight basis as indicated in the examples. Agar is added when a solid medium is desired.

BM₃—Cotyledonary Embryo Development Medium 7541

BM+25 mg/L abscisic acid+8% PEG-8000+1% sorbitol+ 900 mg/L additional myo-inositol+0.125% activated charcoal. 0.3% Gelrite substituted for agar. The following amino acid mixture is added: L-proline—100 mg/L, L-asparagine—100 mg/L, L-arginine—50 mg/L, L-alanine 20 mg/L, and L-serine—20 mg/L.

BM₄—Germination Medium

BM modified by reducing sucrose to 20,000 mg/L, myo-inositol to 100.0 mg/L, glutamine and casamino acids to 0.0 mg/L+0.6% agar and 0.25% activated charcoal.

Stage I—Induction Sterile gametophytes with intact embryos were placed on a solid BM₁ culture medium and held in an environment at 22°–25° C. with a 24 hour dark photoperiod for a time of 3–5 weeks. The length of time depended on the particular genotype being cultured. At the end of this time a white mucilagenous mass had formed in association with the original explants. This appears to be identical with that described by Gupta and Durzan (1987). Microscopic examination revealed numerous early stage embryos associated with the mass. These are generally characterized as having a long thin-walled suspensor associated with a small head with dense cytoplasm and large nuclei. Typical early stage embryos are illustrated in FIG. 1.

Osmolality of the induction medium may in some instances be as high as 170 mM/kg. Normally it will be about 160 mM/kg or even lower. The osmolality of the medium described above was 150 mM/kg.

Figure 2:
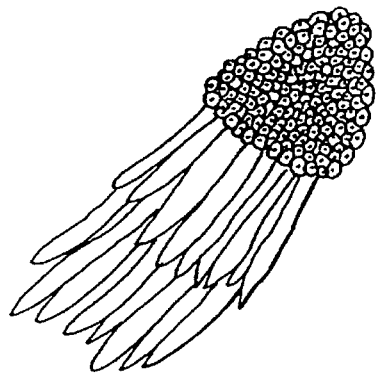
FIG. 2 shows advanced early stage embryos.

Stage II—Maintenance and Multiplication Early stage embryos removed from the masses generated in the induction stage were first placed on a BM₂ gelled maintanance and multiplication medium. This differs from the induction medium in that the growth hormones (both auxins and cytokinins) were reduced by a full order of magnitude. Osmolality of this medium will typically be raised from that of the induction medium to about 180 mM/kg or higher by increasing the concentration of myo-inositol to 0.5% w/v. The temperature and photoperiod were again 22°–25° C. with 24 hours in the dark. Embryos were cultured 12–14 days on the BM₂ solid medium before transferring to a liquid medium for further subculturing. This liquid medium was of similar composition but lacked the gellant. The embryos at the end of the solid maintenance stage were similar in appearance to those from Stage I. After 5 to 6 weekly subcultures on the liquid maintenance medium advanced early stage embryos had formed. These are characterized by smooth embryonal heads estimated to have over 100 individual cells with multiple suspensors, as exemplified in FIG. 2.

Osmotic potential of the maintenance media should typically fall within the range of about 180–400 mM/kg for *Pinus taeda*. Most typically they should be in the neighborhood of about 1.5 times higher than that of the induction or multiplication media. As was noted earlier, the requirements for elevation of osmotic potential at this stage will vary for different species and may vary somewhat even for differing genotypes within a given species.

Stage III—Embryo Development The advanced early stage embryos from Stage II culture were transferred to a solid BM₃ medium. Alternatively, development may be on a saturated pad or similar support on liquid medium. This medium either lacks growth hormones entirely or has them present only at very low levels and has the same lower level of osmoticants as Stages I and II. However, here abscisic acid (5-(1-hydroxy-2,6,6-trimethyl-4-oxo-2-cyclohexen-1-yl)-3-methyl-2,4-pentadienoic acid) appears to be a necessary material for further development. As was noted earlier the further inclusion of an adsorbent material in this medium is highly advantageous. The adsorbent may be chosen from a number of chemical materials having extremely high surface area and/or controlled pore size such as activated charcoal, soluble and insoluble forms of poly(vinyl pyrrolidone), activated alumina, silica gel, molecular sieves, etc. The adsorbent will normally be present in a concentration of about 0.1–5 g/L, more generally about 0.25–2.5 g/L.

Figure 3:
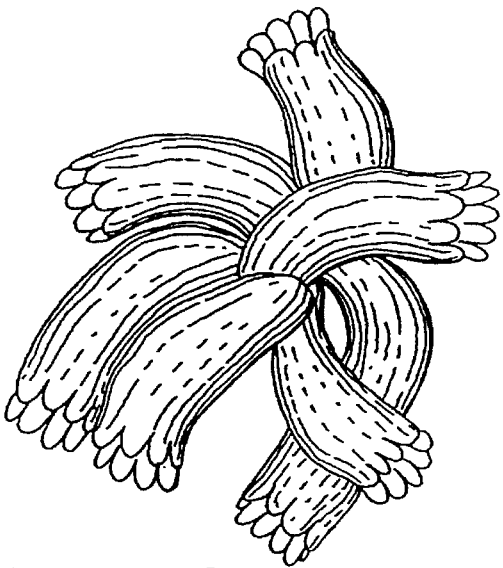
FIG. 3 depicts cotyledonary stage embryos.

The osmotic potential of this medium may be raised substantially over that of the maintenance medium. It has been found advantageous to have an osmolality as high as 300 mM/kg or even higher. As before, development is preferably carried out in complete darkness at a temperature of 22°–25° C. Development time was 5–6 weeks after which elongated cotyledonary embryos 4–5 mm long were present. These appeared as represented in FIG. 3.

Figure 4:
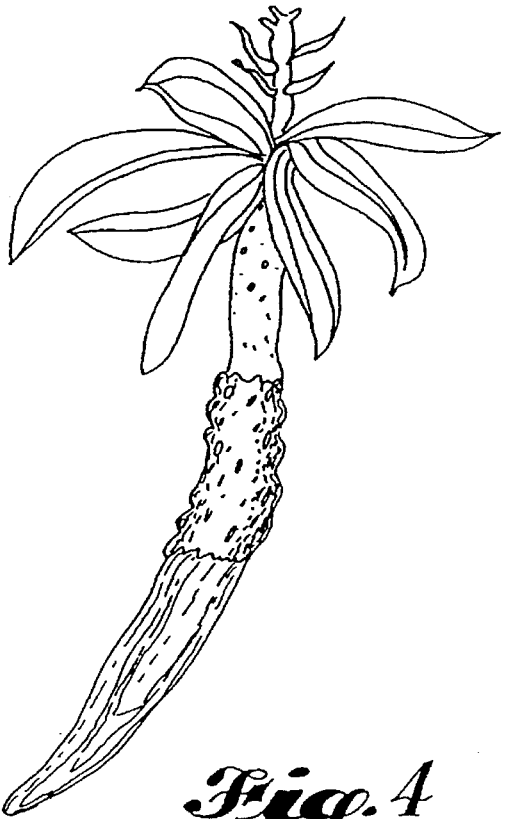
FIG. 4 shows a plantlet ready for transfer to soil.

Stage IV—Germination Cotyledonary embryos from Stage III were placed on solid $BM_4$ medium for germination. This is a basal medium lacking growth hormones which has been modified by reducing sucrose, myo-inositol and organic nitrogen. After about 6–8 weeks under environmental conditions of 23°–25° C. and a 16 hour light/8 hour dark photoperiod the resulting plantlets were approximately 20 mm in length and had a well developed radicle and hypocotyl and green cotyledonary structure and epicotyl. Alternatively, the cotyledonary embryos may be made into artificial seeds as was noted earlier. The young plantlets are shown in FIG. 4.

Because of the reduced carbohydrate concentration, the osmotic potential of the germination medium is further reduced below that of the development medium. It will normally be below about 150 mM/kg and was, in the present example, about 100 mM/kg.

Stage V—Conversion Plantlets from Stage IV were removed from the culture medium and planted in a soil comprising equal parts of peat and fine perlite. Rooting percentage was excellent and the resulting plants showed good growth and vigor.

EXAMPLE 9

In order to see whether the advantageous effects of using maltose in the maintenance medium observed with Douglas-fir and Norway spruce also held true for loblolly pine, the following tests were made. One set of solid and liquid maintenance media was made using 3% sucrose while a similar set of media were made with 3% maltose. Early stage embryos from initiation were placed on each solid maintenance medium for 2 weeks then the resulting mass of embryos was transferred to a corresponding liquid maintenance culture using 20–25 mL of medium in a 250 mL Erlenmeyer flask. After the first liquid culture and thereafter 5 mL of settled cells were transferred to 45 mL of medium After 5–6 weekly subcultures the embryos were examined. The advanced early stage embryos cultured on the maltose media were better singulated and more robust than those cultured on sucrose. They had significantly larger and smoother heads with more elongated suspensors.

The advanced early stage embryos from the maintenance media were then placed on $BM_3$ cotyledonary development medium conbtaining 3% sucrose and otherwise composed as described in Tables 11 and 12 for further development. In this step 1 mL of settled cells was placed on 10 mL of solid cotyledonary development medium. After abour six weeks of culturing, the resulting cotyledonary embryos were compared.

Figure 9:
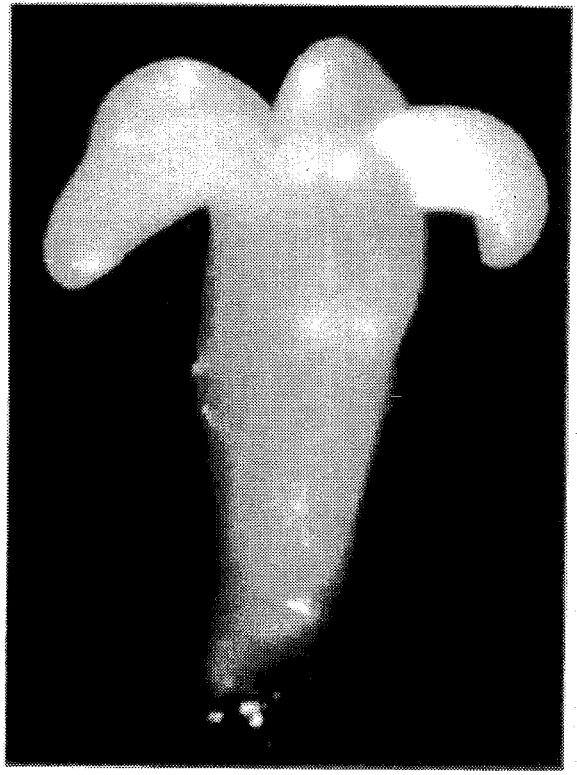
FIGS. 9 and 10 are low power microphotographs of loblolly pine cotyledonary embryos cultured using sucrose and maltose respectively in the maintenance stage.
Figure 10:
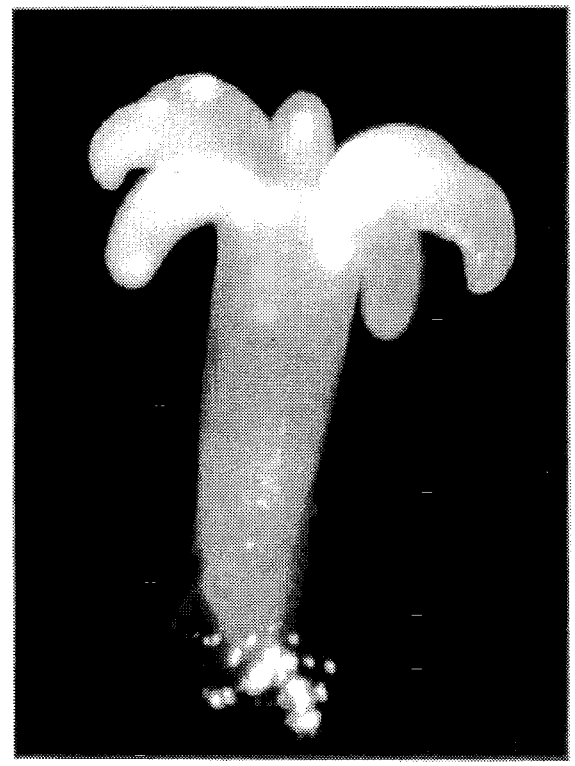

The embryos from the cultures maintained on the maltose containing media (FIG. 10) were significantly improved over those maintained on the sucrose containing media (FIG. 9). The maltose cultured embryos were morphologically more were like zygotic embryos. They were longer and smoother and had more uniform taper, lacking the prominent inflated "waist area" of their sucrose cultured counterparts. Surprisingly, the maltose maintained embryos had a greater number of cotyledons. This is believed to be a definite advantage for germination and conversion since the cotyledons rapidly take over the process of manufacturing nutrients after germination. This also points out the importance of having very strong advanced early stage embryos for subsequent development.

It should be recognized that there is not one single set of culturing conditions that will be suitable for achieving somatic embryogenesis of all species or for all genotypes within a species. Tissue culture as a whole is a highly unpredictable science. This statement has even greater applicability to somatic embryogenesis. Adjustments in the mineral and plant hormone constituents of the culture media must frequently be made depending on the particular species and genotype being cultured. This applies to each of the various stages of culturing from explants to plantlets. These adjustments are considered to be within the routine experimental capability of those skilled in the art of tissue culture. The procedures and formulations reported here have been somewhat modified over those reported earlier as more experience has been gained. They have given results that are far superior in terms of success and consistency than any processes reported heretofore. The procedure using maltose in the maintenance media has been successfully applied to several species and many genotypes of the coniferous plants studied to date and appears to be of general use for all coniferous species.

It will be understood that many variations can be made in the procedures described for the various culturing stages while still remaining within the spirit of the present invention. It is the intention of the inventors that such variations should be included within the scope of their invention if found defined within the following claims.

BIBLIOGRAPHY

Abo El- Nil, Mostafa M.
   1980 Embryogenesis of gymnosperm forest trees. U.S. Pat. No. 4,217,730.

Ammirato, Philip V.
   1977 Hormonal control of somatic embryo development from cultured cells of caraway: interactions of abscisic acid, zeatin, and gibberellic acid. *Plant Physiology* 59: 579–586.

Becwar, Michael R., Emily E. Chesick, Lewis W. Handley III, and Mark R. Rutter
   1995 Method for regeneration of coniferous plants by somatic embryogenesis, U.S. Pat. No. 5,413,390.

Durzan, D. J. and P. K. Gupta
   1987 Somatic embryogenesis and polyembryogenesis in Douglas-fir cell suspension cultures. *Plant Science* 52: 229–235.

Evans, M. L.
   1984 Functions of Hormones at the cellular level of organization. In *Hormonal Regulation of Development II*, Tom K. Scott Ed., pp 23–79, Springer-Verlag, N.Y.

Gupta, Pramod K. and Don J. Durjan
   1985 Shoot multiplication from mature trees of Douglas-fir (*Pseudotsuga menziesii*) and sugar pine (*Pinus lambertiana*). *Plant Cell Reports* 4: 177–179.

1986 Plantlet regeneration via somatic embryogenesis from subcultured callus of mature embryos of *Picea abies* (Norway spruce). In *Vitro Cellular & Developmental Biology* 22: 685–688.

1987 Biotechnology of somatic polyembryogenesis and plantlet regeneration in loblolly pine. *Bio/Technology* 5: 147–151.

Gupta, Pramod K. and Gerald S. Pullman
- 1990 Method for reproducing coniferous plants by somatic embryogenesis. U.S. Pat. No. 4,957,866.
- 1991 Method for reproducing coniferous plants by somatic embryogenesis using abscisic acid and osmotic potential variation. U.S. Pat. No. 5,036,007.
- 1993 Method for reproducing conifers by somatic embryogenesis using stepwise hormone adjustment. U.S. Pat. No. 5,236,841.

Hakman, Inger and Sara von Arnold
- 1985 Plantlet regeneration through somatic embryogenesis in *Picea abies*. *Journal of Plant Physiology* 121: 149–158.

Lakshmi Sita, G.
- 1985 Sandalwood (*Santalum album*). In *Biotechnology in Agriculture and Forestry* 1: *Trees* Y. P.S. Bajaj, ed., Springer-Verlag, N.Y.

Murashihe, Toshio and Folke Skoog
- 1962 A revised medium for rapid growth and bio assays with tobacco tissue cultures. *Physiologia Plantarum* 15: 473–493.

Nagmani, R. and R. J. Dinus
- 1991 Maturation of Douglas-fir somatic enbryos in suspension culture. Paper delivered at the 21st Southern Forest Tree Improvement Conference, Knoxville, Tenn., June 17–20, 1991.

Pullman, Gerald S. and Pramod K. Gupta
- 1991 Method for reproducing coniferous plants by somatic embryogenesis using adsorbent materials in the development stage media. U.S. Pat. No. 5,034,326.

Rangaswamy, N. S.
- 1986 Somatic embryogenesis in angiosperm cell tissue and organ cultures. *Proceedings Indian Academy of Sciences (Plant Sciences)* 96(4): 247–271.

Schuller, Astrid and Gerhard Reuther
- 1993 Response of Abies alba embryonal-suspensor mass to various carbohydrate treatments. *Plant Cell Reports* 132: 199–202.

Sondahl, Maro R., T. B. Sereduk, Claudia M. Bellato, and Zhenghua Chen
- 1988 Somatic embryogenesis and plant regeneration of cacao. European Patent Application A 0 293 598.

Strickland, Steven G., James W. Nichol, Carol M. McCall, and David A. Stuart
- 1987 Effect of carbohydrate source on alfalfa somatic embryogenesis. *Plant Science* 48: 113–121.

Stuart, David A., Steven G. Strickland, and James W. Nichol
- 1989 Enhanced somatic embryogenesis using maltose. U.S. Pat. No. 4,801,545.

Teasdale, Robert D., Pamela A. Dawson, and Harold W. Woolhouse
- 1986 Mineral nutrient requirements of a loblolly pine (*Pinus taeda*) cell suspension culture. *Plant Physiology* 82: 942–945.

Tremblay, Laurence and Francine M. Tremblay
- 1991 Carbohydrate requirements for the development of black spruce (*Picea mariana* Mill. B.S.P.) and red spruce (*P. rubens* Sarg.) somatic embryos. *Plant Cell, Tissue and Organ Culture* 27: 95–103.

Uddin, M. Rafique
- 1993 Somatic embryogenesis in gymnosperms. U.S. Pat. No. 5,187,092.

Verhagen, Shirley A. and Steven R. Wann
- 1989 Norway spruce somatic embryogenesis: high-frequency initiation from light cultured mature embryos. *Plant Cell, Tissue and Organ Culture* 16: 103–111.

I claim:

1. A method for reproducing coniferous somatic embryos by somatic embryogenesis which comprises:
   placing an explant on an initiation culture medium and growing a culture containing early stage embryos;
   transferring the early stage embryos to a maintenance and multiplication medium containing sufficient plant growth hormones and nutrient materials to maintain and multiply said early stage embryos, said nutrient materials comprising maltose as a carbon and energy source whereby the embryos develop into advanced early stage embryos.

2. The method of claim 1 in which the maltose is present in an amount of about 1–6% w/v of the culture medium.

3. The method of claim 1 in which the advanced early stage embryos are further cultured on a cotyledonary embryo development medium in order to produce cotyledonary stage somatic embryos suitable for germination into plantlets.

4. The method of claim 2 in which the advanced early stage embryos are further cultured on a cotyledonary embryo development medium in order to produce cotyledonary stage somatic embryos suitable for germination into plantlets.

5. The method of claim 1 in which the coniferous plants are selected from the family Pinaceae.

6. The method of claim 5 in which the plants are selected from the genera Pinus, Picea, and Pseudotsuga.

7. The method of claim 6 in which the plant is *Pinus taeda*.

8. The method of claim 6 in which the plant is *Pseudotsuga menziesii*.

9. The method of claim 3 in which the plant is *Pseudotsuga menziesii* and which includes the further step, prior to the transfer of the advanced early stage embryos to the development medium, of transferring the embryos to a liquid culture medium containing a sufficient amount of abscisic acid to effect singulation of clumped embryos.

10. The method of claim 9 in which the singulation medium also comprises maltose as the carbon and energy source for the embryos.

11. The method of claim 4 in which the plant is *Pseudotsuga menziesii* and which includes the further step, prior of the transfer of the advanced early stage embryos to the development medium, of transferring the embryos to a liquid culture medium containing a sufficient amount of abscisic acid to effect singulation of clumped embryos.

12. The method of claim 11 in which the singulation medium also comprises maltose as the carbon and energy source for the embryos.

13. A method for reproducing coniferous plants by somatic embryogenesis which comprises:
   placing an explant on an initiation culture medium and growing a culture containing early stage embryos;
   transferring the early stage embryos to a maintenance and multiplication medium containing sufficient plant growth hormones and nutrient materials to maintain and multiply said early stage embryos,
   further transferring said early stage embryos to a second maintenance culture medium having sufficient nutrient materials to support further growth of said embryos to advanced early stage embryos, said nutrient materials comprising maltose as a carbon and energy source;
   again transferring the advanced early stage embryos for culture on a cotyledonary embryo development medium in order to produce cotyledonary stage somatic embryos suitable for germination into plantlets.

14. The method of claim 13 in which the nutrient material in the maintenance and multiplication medium comprises sucrose.

15. The method of claim 13 in which the nutrient material in the maintenance and multiplication medium comprises maltose.

16. The method of claim 13 in which the second maintenance medium contains growth hormones.

17. The method of claim 13 in which the second maintenance medium is essentially free of exogenous growth hormones.

18. The method of claim 13 in which the maltose is present in an amount of about 1–6% w/v of the second maintenance medium.

19. The method of claim 13 in which the coniferous plants are selected from the family Pinaceae.

20. The method of claim 19 in which the plants are selected from the genera Pinus, Picea, and Pseudotsuga.

21. The method of claim 20 in which the plant is *Pinus taeda*.

22. The method of claim 20 in which the plant is *Pseudotsuga menziesii*.

23. The method of claim 20 in which the plant is *Pseudotsuga menziesii* and which includes the further step, prior to the transfer of the advanced early stage embryos to the development medium, of transferring the embryos to a liquid culture medium containing a sufficient amount of abscisic acid to effect singulation of clumped embryos.

24. The method of claim 23 in which the singulation medium also comprises maltose as the carbon and energy source for the embryos.

* * * * *

UNITED STATES PATENT AND TRADEMARK OFFICE
CERTIFICATE OF CORRECTION

PATENT NO. : 5,563,061
DATED : October 8, 1996
INVENTOR(S) : Pramod K. Gupta

It is certified that error appears in the above-identified patent and that said Letters Patent is hereby corrected as shown below:

Column 4, line 1, change "Beewar" to --Becwar--.

Column 8, line 3, change "dumps" to --clumps--.

Column 8, line 21, remove the "," after the word "found".

Column 8, line 34, change "dump" to --clump--.

Column 13, line 10, change "NUC-4386" to --NuC-4386--.

Signed and Sealed this

Twenty-fifth Day of March, 1997

Attest:

BRUCE LEHMAN

*Attesting Officer*     *Commissioner of Patents and Trademarks*